(12) United States Patent
Thielecke et al.

(10) Patent No.: US 7,709,246 B2
(45) Date of Patent: May 4, 2010

(54) DEVICE AND METHOD FOR DETECTING BIOELECTRIC SIGNALS FROM ELECTROPHYSIOLOGICALLY ACTIVE REGIONS IN SPHEROIDS

(75) Inventors: Hagen Thielecke, Blieshostel (DE); Andrea Robitzki, Viernheim (DE)

(73) Assignee: Fraunhofer-Gesellschaft Zur Forderung Der Angewandten Forshung E.V., Munich (DE)

( * ) Notice: Subject to any disclaimer, the term of this patent is extended or adjusted under 35 U.S.C. 154(b) by 1154 days.

(21) Appl. No.: 10/487,711

(22) PCT Filed: Aug. 20, 2002

(86) PCT No.: PCT/EP02/09267
§ 371 (c)(1),
(2), (4) Date: Feb. 26, 2004

(87) PCT Pub. No.: WO03/020125
PCT Pub. Date: Mar. 13, 2003

(65) Prior Publication Data
US 2004/0209351 A1 Oct. 21, 2004

(30) Foreign Application Priority Data
Aug. 30, 2001 (DE) ................................ 101 42 393

(51) Int. Cl.
*C12M 1/34* (2006.01)
*C12Q 1/00* (2006.01)

(52) U.S. Cl. .................. 435/287.1; 435/29; 435/32; 435/288.5; 204/403.1; 205/777.5; 324/450; 324/692

(58) Field of Classification Search .............. 435/287.1, 435/288.4, 288.5, 29, 32; 204/403.1; 205/777.5; 324/450, 692
See application file for complete search history.

(56) References Cited

U.S. PATENT DOCUMENTS
6,122,599 A * 9/2000 Mehta ........................ 702/100

FOREIGN PATENT DOCUMENTS
DE 19946458 A1 * 4/2001
DE 199 53 424 A1 5/2001
GB 2232769 A * 12/1990

OTHER PUBLICATIONS

Molckovsky et al. "Monitoring of cell and tissue responses to photodynamic therapy by electrical impedance spectroscopy." Physics in Medicine and Biology. vol. 46 (Apr. 2001), pp. 983-1002.*
Thielecke et al. 'A multicellular spheroid-based sensor for anti-cancer therapeutics.' Biosensors & Bioelectronics. (Jun. 2001), vol. 16, pp. 261-269.*
A. Molckovsky et al., "Monitoring of cell and tissue responses to photodynamic therapy by electrical impedance spectroscopy", Physics in Medicine and Biology, Apr. 2001, IOP Publishing, UK, vol. 46, No. 4, pp. 983-1002, XP002243462, ISSN: 0031-9155, Abstract 986, figure B.

* cited by examiner

*Primary Examiner*—William H Beisner
(74) *Attorney, Agent, or Firm*—Buchanan Ingersoll & Rooney PC

(57) ABSTRACT

Disclosed is a device for detecting bioelectric signals from spheroids comprising a measuring chamber having a measuring chamber wall which encloses a volume, which is open at least at one side, is composed of an electrically non-conducting material, and has, in at least one measuring region, an inner cross section, which corresponds as far as possible to the largest cross section of a spheroid, comprising at least a number of electrodes which are disposed in a common plane inside said measuring chamber wall and each electrode has a freely accessible electrode surface which is oriented towards the measuring region, and comprising an impedance measuring arrangement which is connected to the electrodes. The device and the method can be used to test substances in 3D biological in-vitro (three-dimensional) cell aggregates.

19 Claims, 6 Drawing Sheets not organized region 11
organized subregion 12
inner fiber layer 13

12 active region
Spheroid 2

$\Delta t_1$
$\Delta t_2$

DEVICE AND METHOD FOR DETECTING BIOELECTRIC SIGNALS FROM ELECTROPHYSIOLOGICALLY ACTIVE REGIONS IN SPHEROIDS

TECHNICAL FIELD

The present invention relates to a device and a method for detecting bioeletric signals from electrophysiologically active regions in spheroids. In particular, it is described how the effect of pharmaceutical preferably neuropharmacological or neurotoxic substances can be detected without damaging the spheroids so that the spheroids continue to be at disposal for further study possibilities.

STATE OF THE ART

In order to be able to routinely determine the effect of substances, for example pharmacological substances, on living systems, in recent years biosensors have been developed, which are based on living cells, see Bousse, L., "Whole Cell Biosensors", Sensors and Actuators, volume 34, pp., 270-275 (1996). Such type biosensors that are based on biological cells are primarily provided with mono-layer cell cultures as a biological detection system, but substance-caused complex cell/cell or cell/matrix interactions can often not be determined with the desired precision and reliability. Furthermore, the effect of neuropharmaceuticals or environmental toxins indeed leads to these complex cell/cell interactions in the central nervous system, which need to be ascertained in order to obtain further insight into the biochemical reaction chain of such substances on biological cell material. Finally, the biosensors based on mono-layer cell cultures have the drawback that the measuring results obtained using them only provide limited information about the actual reaction capabilities of the biological cells, for example to selective application of a substance, because the mono-layer cell cultures do not exist in this from in living nature.

In order to avoid this drawback, biological models approximating an in vivo situation with regard to the intercellular as well as intracellular interactions as closely as possible must be resorted to when studying such type substances. Three-dimensional cell systems reflect an in vivo situation substantially better than single cells or mono-layer cell cultures. Therefore, it is necessary to use three-dimensional cell systems to test substances which are intended for influencing cell/cell interactions.

In order to test the neuropharmacological or neurotoxic effect of substances, for example beyond animal models, bioelectric signals are determined in a prior art manner from the ex vivo tissue sections with the aid of glass micro-electrodes or needle electrodes. Planar electrode arrangements, so-called multi-electrode arrays are utilized to record the signal courses using multi-channel derivations. However, ex vivo tissue sections must be prepared in a very complicated manner from animal models, cannot be standardized and are limited to the existent animals models. Moreover, as ex vivo tissue sections degenerate rapidly, tissue sections are not suited for long-term testing. Long-term testing, however, is of extreme relevance for testing neuropharmaceuticals or environmental toxins and their influence on biological tissue.

An interesting research object for the preceding problem are so-called spheroids, which may be considered as bead-shaped cell aggregates. From literature are known, for example, research in retina genesis and retina regeneration in which such type regenerated bead-shaped cell aggregates, so-called retino-spheroids, are obtained under constant conditions (see Moscona, A. A, "Development of Heterotypic Combination of Dissociated Embryonic Chick Cells", Proc. Soc. Exp. Bio. Med 292, pp. 410-416 (1956); Vollmer, G. Layer, P. G., Gierer, A.: "Reaggreation of Embryonic Chick Retina Cells: Pigment Epithelial Cells Induce a High Order of Stratification", Neurosci. Lett. 48, pp. 191-196 (1984)). These regenerated bead-shaped cell aggregates are reaggregated by suited cultivation of dissociated cells from embryonic retinae.

DE 199 46 458.8 describes a device and a method for characterizing spheroids by means of impedance spectroscopy. The influence of substances on the proliferation, morphology and membrane properties of the in vitro tissue, i.e. outside the living organism, can be determined with this device and method. Locally resolved information from inside the spheroid can, however, not be obtained with this prior-art method. Moreover, information about the intracellular electric potentials in the form of so-called bioelectric signals, from which the effect of pharmaceutical substances, in particular neuro-pharmaceutical or neurotoxic substances can be determined, cannot be obtained with the device described in the preceding printed publication.

SUMMARY OF THE INVENTION

The object of the present invention is to provide a device and a method for detecting bioelectric signals from spheroids in such a manner that it is possible to determine the neurotoxic and neuropharmacological effect of substances on biological tissue by way of in-vitro study as close as possible to the in-vivo situation with regard to intercellular and intracellular interactions.

The solution of the object on which the present invention is based is set forth in claim 1. The subject matter of claim 14 is an inventive method. Features that advantageously develop the inventive idea are the subject matter of the subclaims and are given in the description of the invention with reference to preferred embodiments.

A key element of the present invention is that the device for detecting bioelectric signals from spheroids comprises the following components:

a measuring chamber having a measuring chamber wall, which encloses a volume that is open at least on one side, is made of non-electroconductive material and has an inner cross section at least in one measuring region, which corresponds maximally to the largest cross section of a spheroid.

The measuring chamber is preferably designed as a capillary with capillary walls as well as a capillary bottom, which define the measuring region of the spheroid. The size of the cross section of the measuring region enclosed by the capillary walls is selected in such a manner that the spheroid is in mechanical contact with the measuring chamber respectively capillary wall along the spheroid's biggest circumferential edge in such a manner that the spheroid assumes a fixed as possible spatial position inside the measuring region, which is of great advantage for further measurement of the spheroid. In order to further improve the positioning of the spheroid inside the measuring chamber, respectively the capillary, in a preferred embodiment, the device is connected in the capillary bottom to a partial vacuum conduit to affix the spheroid inside the measuring region by means of suction.

at least a number of electrodes which are disposed in a common plane inside the wall of the measuring chamber, the electrodes each having one freely accessible electrode surface oriented towards the measuring region. The electrodes are preferably disposed in that plane within the wall of the measuring chamber, in which the spheroid comes in contact with the measuring chamber wall with the edge of its greatest circumference. The requirement that the electrodes are disposed in a plane is not necessarily to be understood as mathematically exact, i.e. in the sense of along an imaginary line running around the inner wall of the measuring chamber. The electrodes should be disposed, at least with the surfaces oriented towards the measuring region, along the region of contact between the spheroid and the wall of the measuring chamber in such a manner that the impedance distribution can be detected locally resolved in the cutting plane inside the spheroid predetermined by the electrode configuration with an impedance measuring arrangement that is connected to the individual electrodes. For this purpose, an electric current is induced inside the spheroid via the single electrodes and the diminishing electric voltage over the spheroid is measured. The impedance is formed from the current and the voltage. In order to conduct so-called impedance imaging, the frequency of the current induced in the spheroid is varied over a continuous frequency range, and the impedance yielded as a function of the frequency is recorded. Thus, with the aid of such an impedance imaging system, the tissue parameters can be determined locally resolved inside the cutting plane from the recorded impedance distribution at different frequencies. In this manner, information is gained about the internal structure of the spheroid inside the cutting plane. For instance, so-called electrophysiologically active regions, which may differ in impedance behavior from the other not organized regions inside the spheroid, are distinguished by a subunit with a compact consistency. Especially these electrophysiologically active regions are of particular interest in discovering how certain substances influence biological cells, because it is in these regions that scientifically detectable and evaluatable signals are generated as a sort of cell response to the substance's effect on the respective cell. Electrophysiologically active regions inside the spheroid possess a bioelectrical activity which influences the behavior of the electrical surface potential of the entire spheroid. When there is a change in the bioelectrical activity of the electrophysiological active regions, for example, due to the effect of a certain substance on the spheroid and, therefore, simultaneously on the electrophysiologically active regions, this directly influences the surface potential of the spheroid. Preferably with the aid of a potential determining system, which is connected to the electrodes disposed around the spheroid, it is possible to detect the surface potentials along the cutting plane through the spheroid and to obtain information about the bioelectrical activity of the electrophysiologically active regions inside the cutting plane.

For both impedance measurement and detection of the surface potentials, the free electrode surfaces do not necessarily have to be in direct contact with the surface of the spheroid.

But rather a culture fluid, for example representing a nutrient inside which the spheroid is generated, introduced into the measuring chamber also acts as an electrically conducting medium through which an electrical contact can be produced between the electrodes and the surface of the spheroid.

In a simple embodiment, the free electrode surfaces-connect flush with the inner wall of the measuring chamber in such a manner that a direct contact between the electrode surfaces and the spheroid prevails.

In an alternative embodiment, the electrodes are located in such a manner inside the so-called connecting chambers, which open on one side into the measuring chamber, that the free electrode surfaces are set back from the inner wall of the measuring chamber. The advantage of this is first that the electrodes are easier to exchange respectively replace. Moreover, with suited design and arrangement of the connecting chamber, for example, tapering conically towards the measuring chamber, larger free electrode surfaces can be utilized. With regard to a small as possible phase limit impedance, the use of as large as possible electrode surfaces is desirable, which can be realized by corresponding spaced placement of the inner wall of the measuring chamber inside the conically designed connecting chambers. As already mentioned in the preceding, the culture fluid, which is introduced into the measuring chamber together with the spheroid, acts as an electrical contact medium between the electrodes and the spheroid surface.

With regard, in particular, to studying spheroids in industrial amounts to test how new pharmacological substances act, semiconductor materials are suited for-setting up the device described in the preceding. A multiplicity of array-like arranged measuring chambers, which are adapted in shape and size to studying spheroids and thus permit statistical evaluation due to the great number of examined spheroids, can be realized with the aid of semiconductor technology. A concrete embodiment of this is described in more detail further on with reference to the figures.

With the aid of the preceding device, the spheroids can be studied for their bioelectrical activity without destroying them, to then return them safely to a culture medium for further observation. Thus, one and the same spheroid can be measured several times at intervals in order to be able to determine possible signs of substance-caused degradation. In this manner, conclusions can be drawn statistically about how substances act following evaluation of a multiplicity of such spheroids which are additionally exposed to a certain substance inside a culture medium.

The invented method for detecting bioelectric signals from spheroids is distinguished in particular by the combination of the following method steps: provision of a device of the type described in the preceding, placement and positioning of a spheroid inside the measuring chamber, and conducting an impedance measurement according to the impedance imaging method for locally resolved determination of electrophysiologically active regions in the spheroid. In order to be able to determine any bioelectrical activity, an additional surface potential determination is conducted along the cutting plane predetermined by the configuration of the electrodes.

With the aid of the invented method, the morphology of the multi-cellular spheroids can be determined locally resolved in a non-invasive manner and, moreover, the excitation courses of the electrophysiologically active regions can be precisely determined. The method permits, in particular, to be able to non-invasively detect the effect of substances respectively drugs on 3D in vitro models of the central nervous system. The device, in the sense of a biosensor system described in the preceding, permits the realization of long-term studies of neurotoxic and neuropharmacological effects of substances. The spheroid utilized as a biological detection element is only positioned in the measuring chamber for a short period during impedance measurement and potential determination and can, independent of the measuring arrangement, be cultivated under physiological conditions. Adhesion of the spheroid is largely prevented by the presence of the culture fluid inside the measuring chamber and undesired cell/material interactions are minimized. Depending on the question to be resolved, spheroids or 3D biological detecting elements can be generated with different types of cells in different positions for the biosensor system.

BRIEF DESCRIPTION OF THE DRAWING

The present invention is made more apparent in the following, without the intention of limiting the scope or spirit of the overall inventive idea, using preferred embodiments with reference to the accompanying drawings. Shown is in.

WAYS TO CARRY OUT THE INVENTION, COMMERCIAL APPLICABILITY

Figure 1:
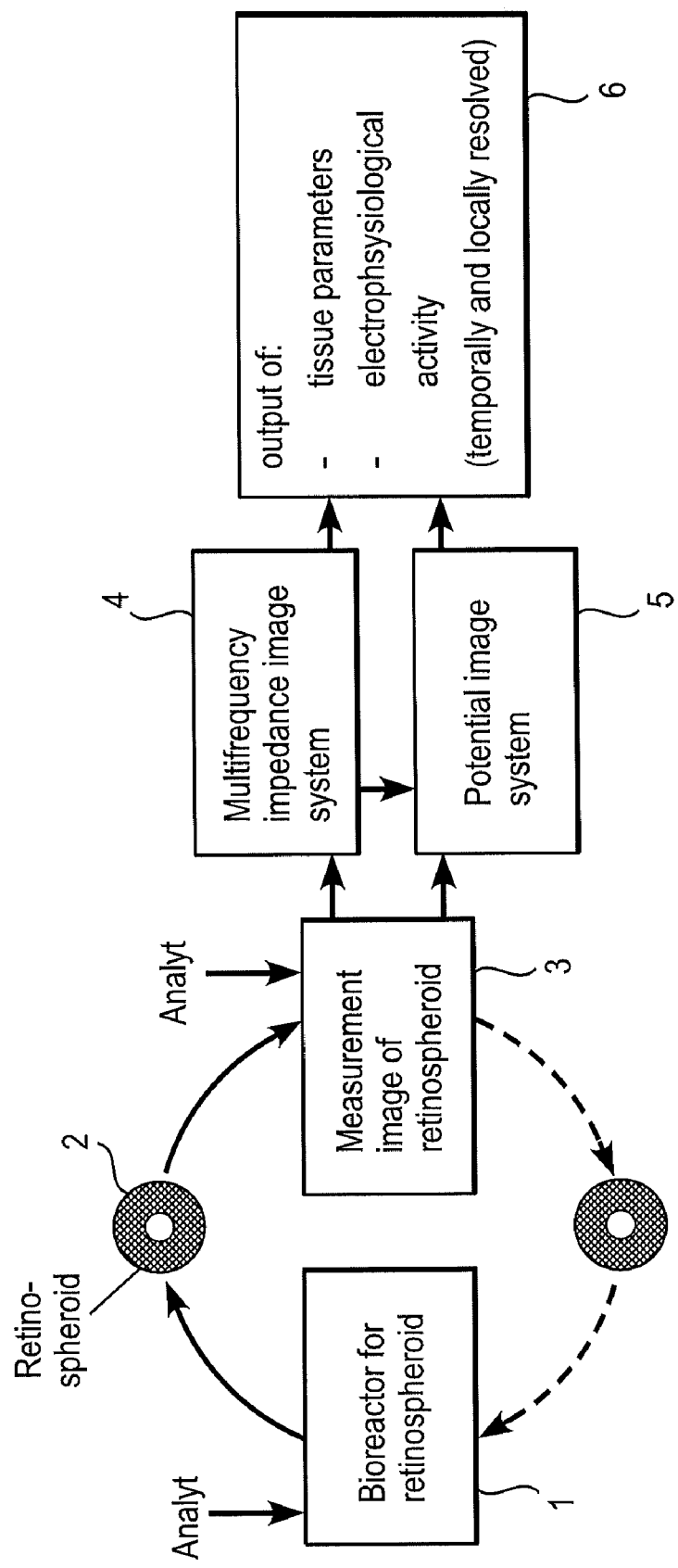
FIG. 1 a schematic flow chart representation of carrying out the method of analysis, FIGS. 2a,b representation of a measuring chamber with a spheroid, FIGS. 3a,b,c representations of cross sections of a spheroid and an-image of the potential, FIG. 4 a cross section of an array-shaped measuring arrangement in semiconductor technology, FIG. 5 measuring arrangement FIG. 6 a cross section of a measuring chamber and FIG. 7 a cross section of an alternative measuring chamber.

The invented method is explained with reference to FIG. 1 using a study of reaggregated retino-spheroids as an example:

Under micro-gravitation conditions in a bioreactor 1, dissociated embryonic cells of the central nervous system are reaggregated to bead-shaped neuronal reaggregation cultures, the so-called retinospheroids. With the addition suited growth factors and/or suited genetic manipulations, it is achieved that electrophysiologically active cell regions form evenly distributed in the spheroid. Thus with high probability, at least one electrophysiologically active region is located in a random cutting plane running through the center of the spheroid.

In order to test the effect of a substance on the spheroid, at least one spheroid 2 has to be isolated from the bioreactor 1 and placed in the measuring chamber of the biosensor system 3 to test it there as an in vitro model. In the bioreactor 1 as well as in the measuring chamber of the biosensor 3, the spheroid 2 is located in a culture fluid, respectively in an analyt, so that the spheroid is replaceable as desired without impairment between the bioreactor and the measuring chamber.

By means of multi-frequency impedance imaging 4, the position and the extension of the various cell regions is determined in a cross section plane predetermined by the electrode configuration inside the measuring chamber. And then the bioelectrical activity of the individual cell regions in the cutting plane is detected by means of the electrical source-imaging 5. Systems and algorithms for the impedance imaging and the electric source imaging are fundamentally known from medical tomography, see Webster, J. G., "Electrical Impedance Tomography", Adam Hilger, Bristol (1990).

Changes in the electrophsiological activity of certain regions in the spheroid, correlation of the electrophysiological activity of different regions and the change in the tissue parameters serve as parameters 6 for the effect of substances on the in vitro tissue model.

Figure 2B:
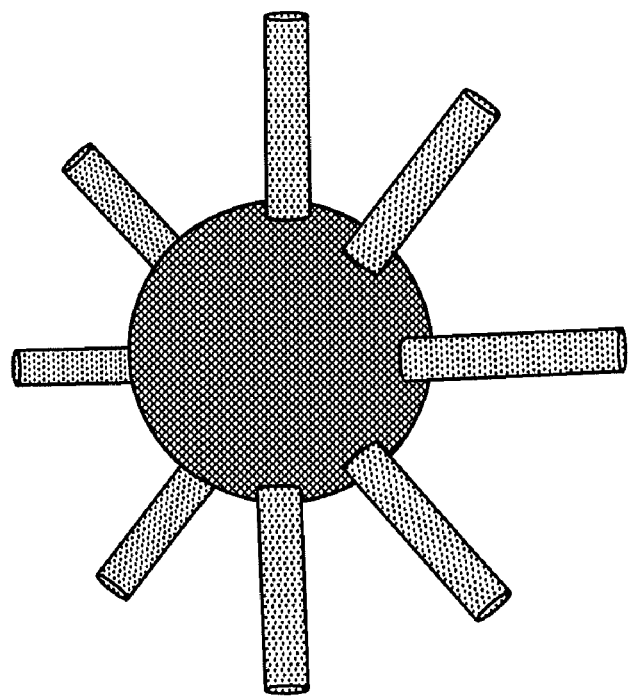
Figure 2A:
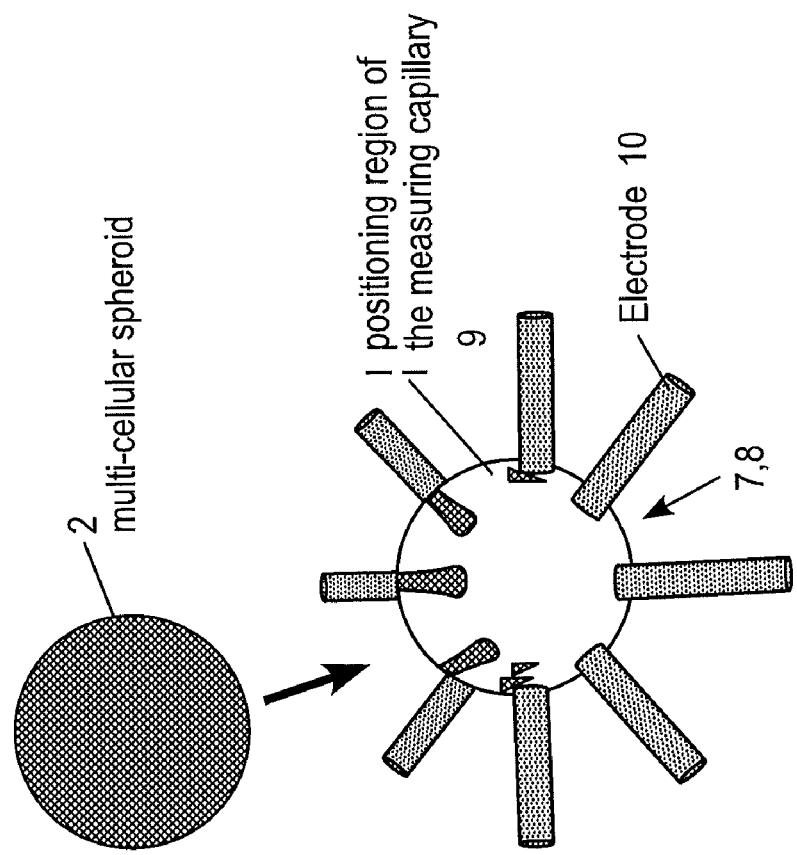

To conduct the impedance imaging and the potential determination, an electrophysiologically active spheroid 2 according to FIG. 2 is positioned in the desired culture stage in a measuring chamber 7. Depending on the question to be resolved, such as for example long-term studies or dynamic excitation, the to-be-tested substance is added to the culture fluid in the bioreactor or to the culture fluid in the measuring chamber 7. The measuring chamber 7 is preferably formed by a capillary 8, which is designed cylindrical in the positioning region and its wall 9 is made of an electrically insulated material. In the positioning region of the capillary 8, a multiplicity of electrodes 10 are disposed in the capillary wall 9 in at least one plane perpendicular to the longitudinal axis. As the electrodes 10 with their free electrode surfaces in the preferred embodiment shown in FIGS. 2a,b are placed flush with the inside wall of the measuring chamber, they come in contact with the spheroid (2) placed inside the measuring chamber in a cutting plane along the spheroid's greatest circumference (FIG. 2b). The electrodes are electrically contacted singly from the outside for triggering (not depicted).

This arrangement is used both for locally resolved determination of the passive electrical properties of the in-vitro tissue and for determination of the spatial and temporal course of the electrophysiological excitation.

Figure 3A:
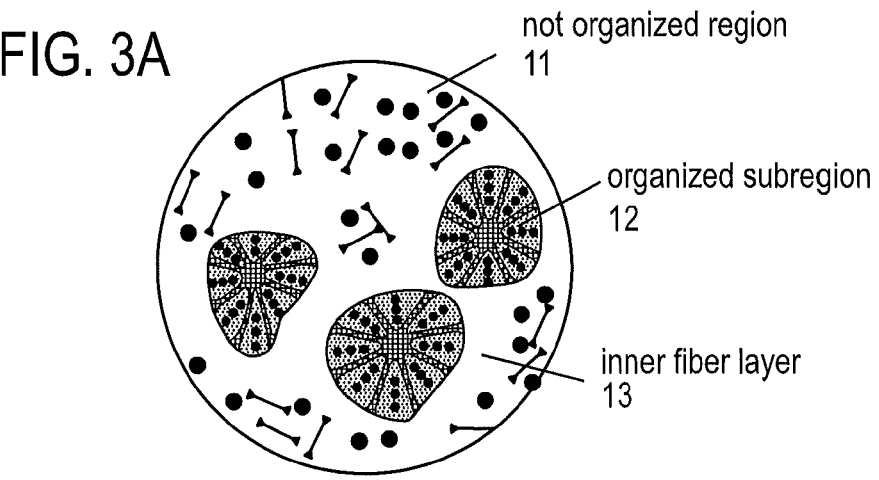
Figure 3B:
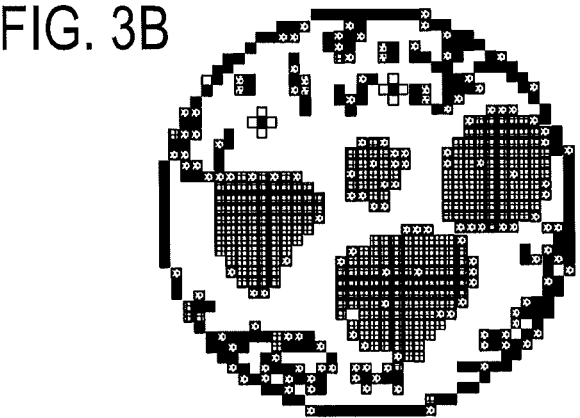
Figure 3C:
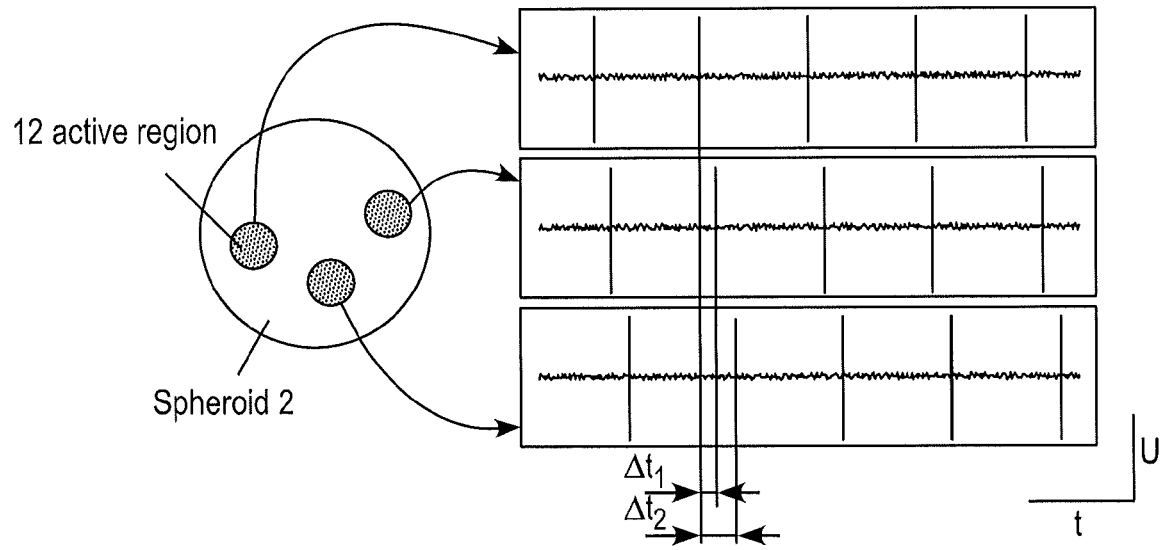

In order to determine the impedance distribution in the cutting plane of the spheroid in which the electrodes lie, the electrodes are connected in a suited manner with an impedance imaging system. The tissue parameters are determined locally resolved from the impedance distributions at different frequencies. FIG. 3a shows an actual section through a spheroid with the usually not further organized regions 11, organized subregions, the so-called electrophysiologically active regions 12 and inner fiber layers 13. FIG. 3b shows a section image determined by means of impedance imaging, which really corresponds to the section image shown in FIG. 3a. The bioelectrical activity of certain regions is determined from the surface potentials, which are determined with the electrodes, and from the impedance distribution, see diagrammatic representation in FIG. 3c. In the determination of the surface potentials, the electrodes of the measuring capillaries are connected to a measurement system. Marked evaluatable measured signals are, in particular, the voltages peaks perceivable on the surface of the spheroid (see diagrammatic representation) and their temporal sequence ($\Delta t_1$, $\Delta t_2$). In particular, these measured values are the ones that are provenly influenced by the presence of certain substances, which allows drawing conclusions about the effect of certain substance on biological material.

Figure 4:
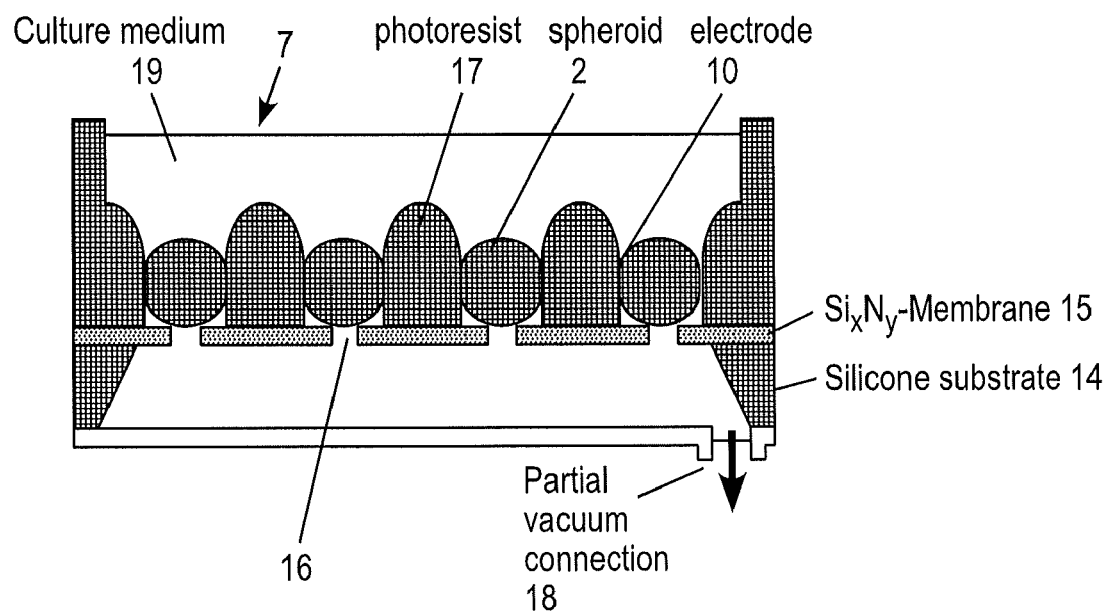

FIG. 4 shows a measuring chamber arrangement in which a multiplicity of single measuring chambers 7 is disposed in an array structure on a planar substrate 14. In order to produce such a measuring chamber arrangement, a silicon nitride layer 15 with a thickness of approximately 1 µm is deposited on a silicon substrate 14. The silicon nitride layer 15 is exposed from the underside as membranes. Furthermore, microholes 16 with a diameter of 20 µm are produced in the membrane 15 by means of dry etching. Finally, a phototresist 17 with a thickness of 40 µm is applied. Cylindrically shaped measuring chambers 7 (diameter of 150 µm) are etched free into the photoresist 17 concentric to the microholes. A metal layer with a thickness of 10 µm is deposited onto the photoresist 17 and structured in such a manner that the measuring chambers 7 are surrounded by eight electrodes 10 disposed evenly spaced in a circle. Finally another photoresist layer 17 (50 µm) is deposited and structured.

In order not to damage the spheroids when placing them into the individual measuring chambers 7, the edges of the measuring chambers 7 are rounded off. In order to be able to apply a partial vacuum 18 for positioning the spheroids, the finished microstructure is glued onto a plate with a borehole and tube connection. To conduct a measurement, the entire region of the measuring chamber 7 is filled with culture fluid 19 to prevent adhesion effects between the individual spheroids and the measuring chamber wall.

Figure 5:
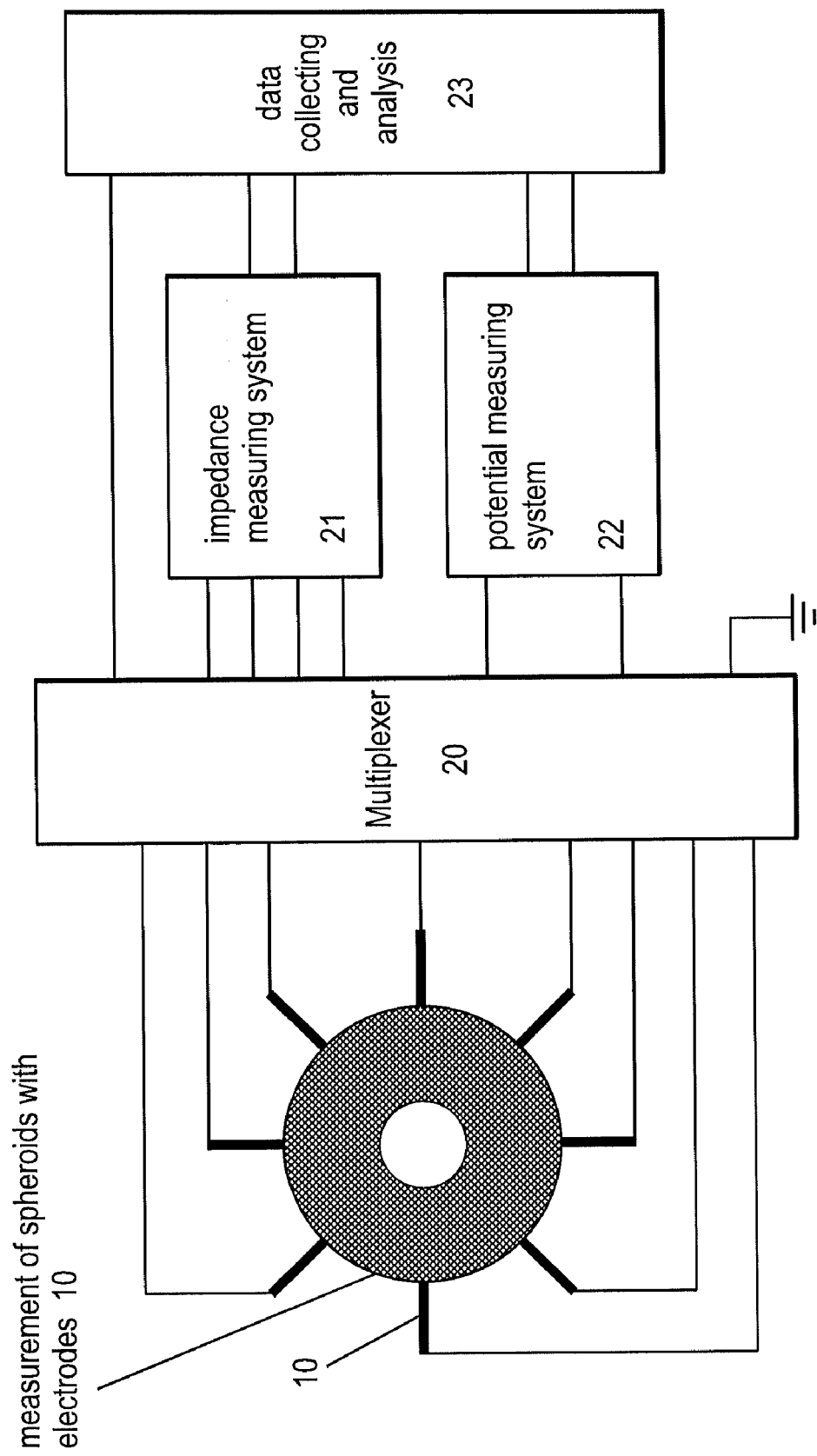

The electrodes 10 placed in the measuring chamber, according to FIG. 5, are connected with an impedance measuring system 21 and a potential determination system 22 via a multiplexer 20. The measured data are transmitted to a data collection and data analysis unit 23, which also controls the multiplexer 20.

Figure 6:
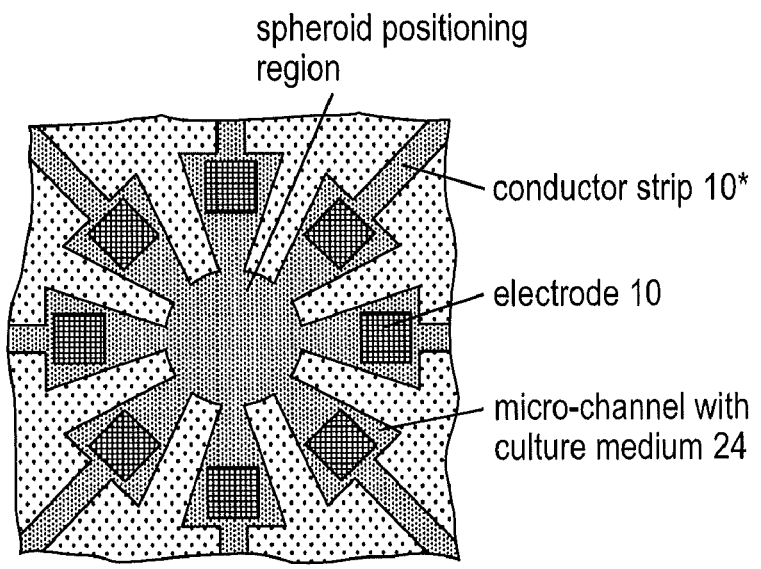

According to the preferred embodiment in FIG. 6 showing a cross section of a measuring chamber 7, connecting chambers 24, which end in the measuring chamber, are disposed in a star-shaped manner running conically into the measuring chamber 7. In this way, the size of the metal electrodes 10, which are each contacted by strip conductors 10\*, can be selected independent of the size of the measuring chamber, and the phase limit impedance of the electrode 10 can be reduced by larger electrode surfaces.

Figure 7:
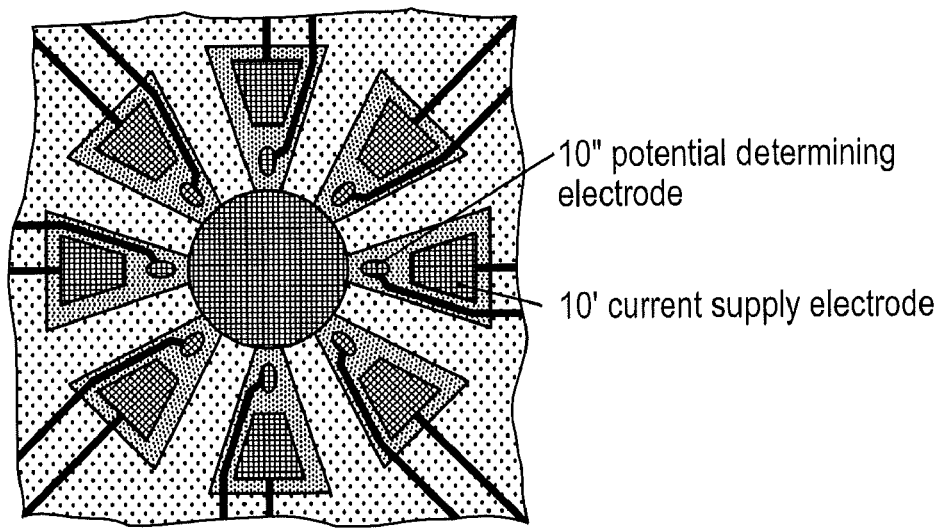

In another preferred embodiment according to FIG. 7, in order to realize impedance measurements, one electrode 10' for supplying current and one electrode 10" for determining the potential are disposed in each channel in a four-electrode configuration.

LIST OF REFERENCE NUMBERS 1 bioreactor
2 spheroid
3 biosensor, measuring arrangement
4 impedance measuring arrangement
5 potential determining arrangement
6 evaluation parameter
7 measuring chamber
8 capillary
9 measuring chamber wall
10 electrode
10* strip conductor
10' current supply electrode
10" potential determining electrode
11 not organized region
12 organized region, electrophysiological region
13 inner fiber layer
14 substrate
15 membrane
16 microhole
17 photoresist
18 vacuum connection
19 culture fluid
20 multiplexer
21 impedance system
22 potential determining system
23 data collection and analysis system
24 connecting chamber

What is claimed is:

1. A device for detecting bioelectric signals from spheroids comprising a measuring chamber that is pot-shaped, said measuring chamber having a measuring chamber wall which encloses a volume which is open at one side, wherein the measuring chamber is composed of an electrically insulating material and has, in at least one measuring region, an inner cross section which corresponds to the largest cross section of a spheroid and is sized such that the spheroid is in contact with the measuring chamber wall, at least a number of electrodes which are disposed in a common plane inside said measuring chamber wall and each said electrode has a freely accessible electrode surface which is oriented towards said measuring region, and an impedance measuring arrangement which is connected to said electrodes.

2. The device according to claim 1,
   wherein a potential determining system is connected to said electrodes.

3. The device according to claim 2,
   wherein provided in said measuring chamber wall is a number of connecting chambers which are openly connected with said measuring region and are disposed in a common plane evenly distributed around said measuring region in circumferential direction, and
   inside each of said connecting chamber an electrode is placed,
   whose said freely accessible electrode surface oriented towards said measuring region is spaced at a distance from said measuring chamber inner wall.

4. The device according to claim 3,
   wherein a second electrode is arranged inside each of said connecting chambers and being connected to said potential determining system.

5. The device according to claim 2,
   wherein said impedance measuring arrangement and said potential determining system are connected to said electrodes via a multiplexer.

6. The device according to claim 2,
   wherein a data collecting and data evaluation unit is connected to said impedance measuring arrangement as well as to said potential determining system.

7. The device according to claim 1,
   wherein said measuring chamber is designed as a cylindrical capillary, and said at least a number of said electrodes is disposed in one plane orthogonally to the length of said capillary.

8. The device according to claim 1,
   wherein said freely accessible electrode surfaces of said electrodes are designed flush with said measuring chamber inner wall.

9. The device according to claim 1,
   wherein said measuring chamber can be filled with an electrically conducting liquid.

10. The device according to claim 1,
    wherein a partial vacuum conduit is connected to said measuring chamber.

11. The device according to claim 1,
    wherein a partial vacuum conduit is provided at the bottom of said pot for positioning and attaching a spheroid placed in said pot-shaped measuring chamber by means of a partial vacuum.

12. The device according to claim 1,
    wherein a multiplicity of measuring chamber is arranged in an array-like manner and is designed in planar semiconductor substrate technology.

13. The device according to claim 1,
    wherein said electrodes are disposed evenly distributed in circumferential direction of said measuring chamber wall.

14. A method for detecting bioelectric signals from spheroids through a device that includes a measuring chamber that is pot-shaped, said measuring chamber having a measuring chamber wall which encloses a volume which is open at one side,
    wherein the measuring chamber is composed of an electrically insulating material and has, in at least one measuring region, an inner cross section which corresponds to the largest cross section of a spheroid and is sized such that the spheroid is in contact with the measuring chamber wall, at least a number of electrodes which are disposed in a common plane inside said measuring chamber wall and each said electrode has a freely accessible electrode surface which is oriented towards said measuring region, and an impedance measuring arrangement which is connected to said electrodes, the method comprising:

placing and positioning a spheroid inside said measuring chamber, and conducting an impedance measurement based on a locally resolved determination of electrophysiologically active regions in said spheroids.

15. The method according to claim 14,
wherein a surface potential determination is conducted for detecting said bioelectrical activity.

16. The method according to claim 14,
wherein said impedance measurement is conducted at different triggering frequencies to obtain an impedance spectrum.

17. The method of claim 14, wherein
the measuring chamber includes a culture fluid, and the free electrode surfaces are placed flush with the measuring chamber wall, the method comprising:
individually contacting each electrode from outside the measuring chamber.

18. A method for detecting bioelectric signals from spheroids through a device that includes a measuring chamber that is pot-shaped, said measuring chamber having a measuring chamber wall which encloses a volume which is open at one side, wherein the measuring chamber is composed of an electrically insulating material and has, in at least one measuring region, an inner cross section which corresponds to the largest cross section of a spheroid and is sized such that the spheroid is in contact with the measuring chamber wall, at least a number of electrodes which are disposed in a common plane inside said measuring chamber wall and each said electrode has a freely accessible electrode surface which is oriented towards said measuring region, and an impedance measuring arrangement which is connected to said electrodes, the method comprising:

removing a spheroid to which a substance has been applied from a culture medium and placing said spheroid in said measuring chamber of said device;

performing at least one of an impedance measurement and a potential determination non-invasively on said spheroid; and returning said spheroid unharmed to said culture medium.

19. The method according to claim 18,
wherein said substances are pharmaceutical substances, in particular, neuropharmacological or neurotoxic substances.

* * * * *